US007089498B1

(12) United States Patent
Rathjen et al.

(10) Patent No.: US 7,089,498 B1
(45) Date of Patent: Aug. 8, 2006

(54) METHOD FOR PREPARING AND USING PERSONAL AND GENETIC PROFILES

(76) Inventors: Alicemarie G. Rathjen, 3419 Sacramento St., San Francisco, CA (US) 94118; Jacquelyn C. Appell Wheeler, 909 Alvarado #6, Davis, CA (US) 95616; Ronald M. Green, Box 418, Norwich, VT (US) 05055; Xavier Thomas, 1577 F Pershing, San Francisco, CA (US) 94129; Keith A. Dieterich, 1919 Octavia St. Apt. #6, San Francisco, CA (US) 94019; John R. Harding, 2199 Divisadero St., San Francisco, CA (US) 94115; Lois S. Harding, 2199 Divisadero St., San Francisco, CA (US) 94115; William Kimmerly, 5909 Gleam Ct., Agoura Hills, CA (US) 91301; Jack L. Strauss, 2500 Kettering Tower, Dayton, OH (US) 45423; Alex Fordyce, 16 Lower Alctraz Pl. #4, Mill Valley, CA (US) 94941

( * ) Notice: Subject to any disclaimer, the term of this patent is extended or adjusted under 35 U.S.C. 154(b) by 744 days.

(21) Appl. No.: 09/962,985

(22) Filed: Sep. 24, 2001

Related U.S. Application Data

(60) Provisional application No. 60/235,434, filed on Sep. 26, 2000.

(51) Int. Cl.
*G06F 3/00* (2006.01)
*G06F 9/00* (2006.01)
*G06F 17/00* (2006.01)

(52) U.S. Cl. .......................... 715/741; 345/589; 435/6
(58) Field of Classification Search .................. 435/6; 705/1; 713/201; 707/10; 345/794, 793, 345/771, 805, 589; 715/741
See application file for complete search history.

(56) References Cited

U.S. PATENT DOCUMENTS

| | | | | |
|---|---|---|---|---|
| 5,876,933 | A * | 3/1999 | Perlin | ............................ 435/6 |
| 6,366,915 | B1 * | 4/2002 | Rubert et al. | ................. 707/10 |
| 6,640,211 | B1 * | 10/2003 | Holden | .......................... 705/1 |
| 6,691,232 | B1 * | 2/2004 | Wood et al. | ................ 713/201 |

OTHER PUBLICATIONS

Stricher, Johannes, "Computer-based three-dimensional visualization of developmental gene expression" May 2000.*

* cited by examiner

*Primary Examiner*—Steven Sax
*Assistant Examiner*—Boris Pesin
(74) *Attorney, Agent, or Firm*—Min, Hsieh & Hack LLP

(57) ABSTRACT

Method and system for preparing a personal genetic profile includes collecting genetic data from an individual, assigning the data to a coordinate system, storing the data, and providing access for retrieval by the individual from whom the genetic data were collected, after receipt of an Identifier that adequately authenticates the identity of the data requester. Locations of genetic markers are provided as three-dimensional coordinates, described with matrix relationships that are consistent with the primary and secondary chemical structure of molecular constituents of a DNA chain for the individual.

15 Claims, 4 Drawing Sheets

METHOD FOR PREPARING AND USING PERSONAL AND GENETIC PROFILES

This invention claims the benefit of provisional application No. 60/235,434, filed Sep. 26, 2000.

FIELD OF THE INVENTION

This invention broadly relates to genetic testing, and more particularly relates to providing results of private and anonymous genetic testing that can be securely accessed on a network.

Most information about advancements in the biotechnology industry and the mapping of the human genome is written for scientists or medical professionals and is difficult for lay people to even read, let alone understand. Consumers know that these topics are relevant and important, but consumers are uncertain how these topics impact their lives and do not have easy access to the answers. Most importantly, when consumers do become aware that genetic testing is an important tool for managing one's health care and making life decisions, customers are wary of such testing for fear that access to their genetic information will result in discrimination in medical insurance, employment education, and housing.

What is needed is a system that provides results of genetic testing that can be accessed only through presentation and authentication of a confidential identifier or key that is optionally known only to the data owner (e.g., subject of the testing).

SUMMARY OF THE INVENTION

In one aspect of the invention, a method for preparing a personal genetic profile includes collecting genetic data from an individual, assigning the data to a coordinate system, storing the data, and providing access for data retrieval by the individual from whom the genetic data were collected, if the individual is an adult, or from the individual's guardian or parent if the individual is a minor or has a legally appointed representative. The stored data are preferably retrieved through a database and network and may be visually examined by the individual.

In a preferred embodiment for practicing the invention, one collects a DNA sample from oneself, preferably in a non-invasive fashion such as by means of an inner cheek swab, saliva sample, fingernail or hair clippings, and the like. A sample submission kit may be provided for collecting the sample. The kit preferably includes instructions for delivering the sample to a test facility and may also provide an identifier for the sample. Identification may include use of a bar code, serial number, or password. The kit also includes the ability to specify the gene (or disorders associated with genes) for which the user wishes to be tested. The test facility isolates the DNA, standardizes and archives it, and performs the specified tests. The results of the requested tests are stored in machine-readable form together with one or more unique user identifiers, such as a serial number and password or a biometric indicium. The results of the tests are preferably converted to a vector format having two or three location coordinates. The user is then able to utilize a network, provide the user's serial number and authentication indicium, and access his or her data, which can be interactively visualized using the mapping coordinates and vector format of the data.

Visualization of the data preferably utilizes Geographic Information Systems ("GIS") software. Thus, the information of an individual's genetic profile displayed on a secured database can be displayed in multiple views representing different levels of complexity, from a macro view of the 23 pairs of human chromosomes to a micro view at the level of linear array of individual nucleotides or DNA bases. An individual can click on particular markers to link direct to information about that marker, or information about diseases or conditions linked to the indicated marker, and obtain latest industry information, including gene therapies, that are available to work with that marker.

DESCRIPTION OF BEST MODES OF THE INVENTION

Figure 1:
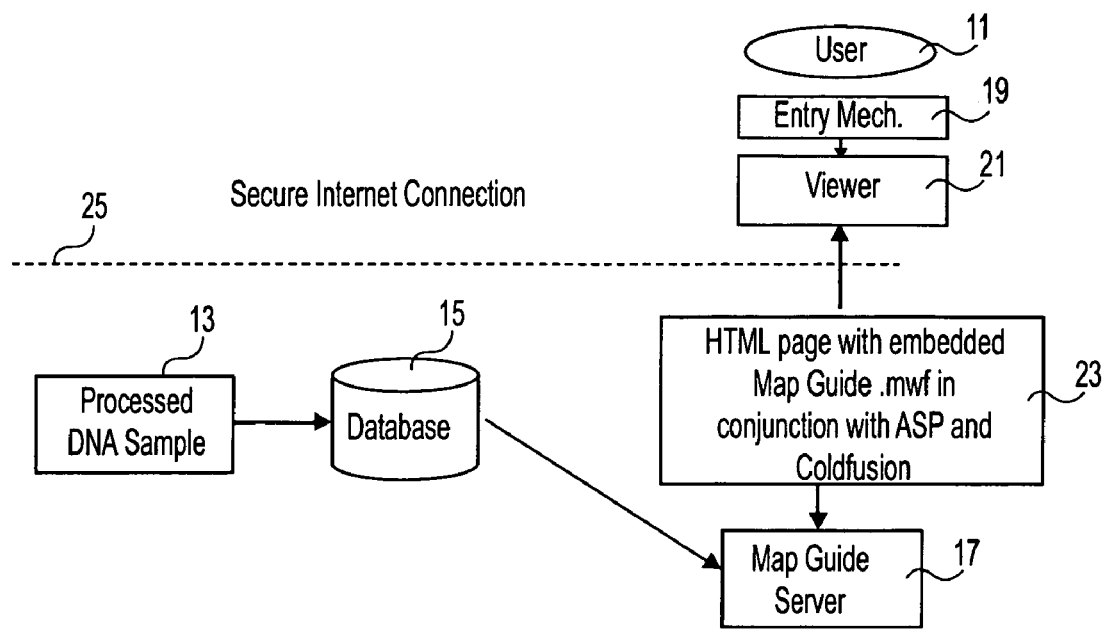
FIG. 1 schematically illustrates a system for practice of the invention.

Practice of the invention preferably begins with the use of a collection kit by which the user collects a DNA sample 13 from himself or herself in a non-invasive fashion. With reference to FIG. 1, a user 11 indicates the gene or disorder for which testing is desired, and the system compares selected characteristics associated with one or more gene markers of the user with corresponding characteristics for the same gene marker(s) as determined from a reference database 15. Optionally, this includes statistics and/or confidence levels associated with different expressions of a particular characteristic associated with one or more such genes. Optionally, part or all of the user's own data are selectively and anonymously added to the reference database 15.

The user 11 requests information on, and a comparison of, a specified organ, tissue, regulatory system or other medical feature, or specifies a particular malady or disease. This may be accomplished by entering queries and/or data in to a Map Guide Server 17, using a keyboard or other data/command entry mechanism 19 and associated viewer 21 that communicate with the Server through an HTML page with embedded Map Guide 23 and a secure Internet connection 25. In response to receipt of the user's query or command, the Map Guide Server queries the database 15, and determines and assembles the relevant data for comparison with the user's data and, optionally, for estimation of confidence levels associated with different plausible results or conclusions, based on the data presented by the user. An array of user data associated with one or more gene markers may be consistent with one or more conclusions, with each such conclusion having its own confidence level(s).

Figure 2:
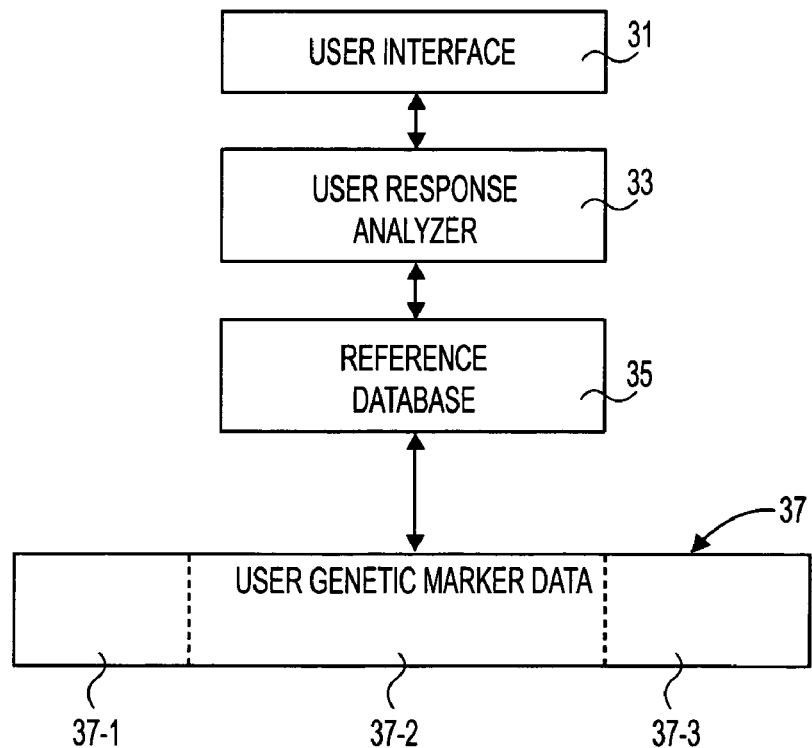
FIG. 2 illustrates a sequence of layers of response to a user's query in practicing the invention.

FIG. 2 is a schematic view of several layers of response to a user's query. At a first (highest) layer 31, a user interface receives the user's data/command, optionally in response to user answers or responses to a sequence of questions posed by an expert system or other user interrogation system. At a second layer 33, the system analyzes the user answers and responses and determines if the reference database (13 in FIG. 1) has any relevant information. For example, if the user's queries and commands concern a neuropathological response to a little known substance or to a rare and acute health event, the system may advise the user that this database, at present, has no information that is relevant to the user's problem.

If the system determines, from the user's answers and responses, that some information contained in the database is relevant to the user's problem, the reference database is now queried, at a third layer 35, to assemble the relevant information. At a fourth layer 37, the system receives and analyzes the user data and compares the user data with corresponding gene marker data or other data and determines confidence levels for one or more results or consequences that are relevant to the user data presented.

Optionally, access to the fourth layer 37 requires presentation of authentication of the identity of the requester, using one or more of a password, a physical or electronic token, and one or more biometric indicia. The fourth layer 37 is optionally divided into two or more sub-regions 37-k (k=1, 2, . . . ), as illustrated in FIG. 2, which may be overlapping or may be mutually exclusive, with access to each sub-region requiring presentation of different authentication and being available to a different group of one or more physicians and health care professionals. Access to a particular sub-region in the fourth layer requires a "need to know" the particular information contained in that sub-region. For example, an osteopathic physician may have no need to know details concerning effects of a psychotropic drug currently being taken by the owner of the data in the fourth layer. In one embodiment, only the owner of the data, as a "super user" has access to all sub-regions within the fourth layer 37.

More than 740 disorders associated with specific genetic profiles have already been identified. Initially, testing is provided for selected markers, for example, Fragile X and Hemochromatosis, and a database of identified and important markers is accumulated. As data on each additional marker are added to a reference database, the corresponding marker in a patient can be examined and compared with information in this database.

Fragile X is a genetic condition that results in learning disabilities in children. It is very useful for parents to know about the presence of this condition as early as possible so that the parents can plan for the extra tutoring and educational attention that such a child will require. Fragile X is being considered for mandatory testing at birth and is already widely accepted as an important, non-controversial test.

Hemochromatosis, a common genetic disorder in the United States, causes the body to accumulate too much iron, a condition that is typically overlooked or misdiagnosed but can lead to serious liver damage and other health complications if left unchecked. The advantage of testing for this condition genetically is that is remarkably easy to prevent: individuals need only to donate blood regularly to avoid the onset of symptoms and to maintain health.

Other illustrative conditions for which tests can be conducted include the following disorders which are associated with specific genetic profiles: colon cancer, osteoporosis, glaucoma, cataracts, breast cancer, melanoma, diabetes, prostate cancer, hypercholesterolemia, dyslexia, and malignant hyperthermia.

Further, if one wishes to have a genetic "fingerprint," for example, of one's child or children, a test employing about 100 DNA markers, distributed randomly throughout the genome, can be performed. These common markers, referred to as single-nucleotide polymorphisms or SNPs (pronounced "snips"), are present at about one site in a thousand in the DNA in a human genome. These random markers provide a cost-effective approach to map on a DNA sample with current technologies. One hundred markers of moderate frequency in the population would uniquely identify every individual on Earth, with virtually no chance of misidentification or confusion.

Because the amount of DNA obtained from a typical specimen is sufficient to perform several individual gene marker tests, the user likely will not need to resubmit a DNA sample if he or she desires additional genetic tests.

The genetic testing can be performed by various assay technologies known and used by persons skilled in the art. As one example, Sequenom, based in San Diego, Calif., has developed single-nucleotide polymorphism genotyping technology that is based on MALDI-TOF mass. Another example is Orchid Bioscience based in Princeton, N.J., which offers an assay called genetic bit analysis (GBA). Another example is Amersham Pharmacia Biotech, based in Cardiff, United Kingdom, which has an assay called rolling circle amplification from Molecular Staging, located in Guildford, Conn. Each of these companies is developing an integrated instrumentation package to support high throughput assays. Included in the Amersham package is an integrated lab information management system (LIMS) and Oracle database, optionally including bar code reading capability. Several reliable commercial technologies are available for measuring SNPs in a cost-effective manner.

Depending on the tests to be performed, there will be a varying number of genotypes required. Testing for Hemochromatosis, for example, will likely require examination of about eight genotypes.

An important aspect of one embodiment of the invention is that the individual submitting the sample will have sole access to his or her genetic information (or, in the case of a parent, to the dependent child's information), as well as control over its disclosure, use and/or disposition. Optionally, and within reasonable limits, this individual will determine whether a health record concerning this individual will be retained or deleted/destroyed.

In one embodiment, an Identifier can be a four color, two-dimensional array of uniform objects, such as triangles, rectangles, polygons, circles or ovals, that will represent an individual's genetic identity. The array dimensions may be 14×14 objects (more generally, with M1×M2 objects), or a total of 196 array objects. These 196 array objects, arranged in a selected pattern, will represent the two alleles (or genetic variants) at 98 distinct genetic loci that vary at a single DNA base in the human population. Genetic markers of this case are referred to as SNPs. The color of each array object can indicate a genotype or allele. For example, yellow can represent guanine base or G, blue can represent cytosine base or C, green can represent adenine base or A, and red can represent thymine or T.

A selected number N genetic markers (e.g., N=8), preferably in an agreed order, is established. In one embodiment, the markers in the marker set meet the following criteria: (1) no two markers can be linked by more than 10 centimorgans genetic distance, assuming a total of 3000 centimorgans genetic distance for the entire human genome; (2) no markers from the X or Y chromosome are included, to avoid gender identification being implicit in use of an Identifier; (3) all markers are bi-allelic; any markers known to be tri-allelic or tetra-allelic within the general population are preferably excluded from the marker set; and (4) the average frequency of the major allele of all N loci does not exceed 75 percent in the general human population. A marker set of this specification can uniquely identify one in over three trillion individuals.

The 14×14 object array (or, more generally, M1×M2 object array) represents consecutively the two alleles of the N markers in an established order described above. In the case of heterozygous genotypes of any marker, the alleles are optionally indicated in alphabetical order (i.e., AT, AC, AG, CG, CT, and GT).

The 14×14 object array of colored uniform objects may be used as a visual unique identifier, and it may be stylized and personalized by its owner as a personal logo. The array may be digitized and represented as an array of characters (e.g., A. C, G and T) or numbers (1, 2, 3, . . . , M), and thus may also be used as an electronic identifier for internet security purposes. The Identifier is preferably part of the security mechanism.

Figure 3:
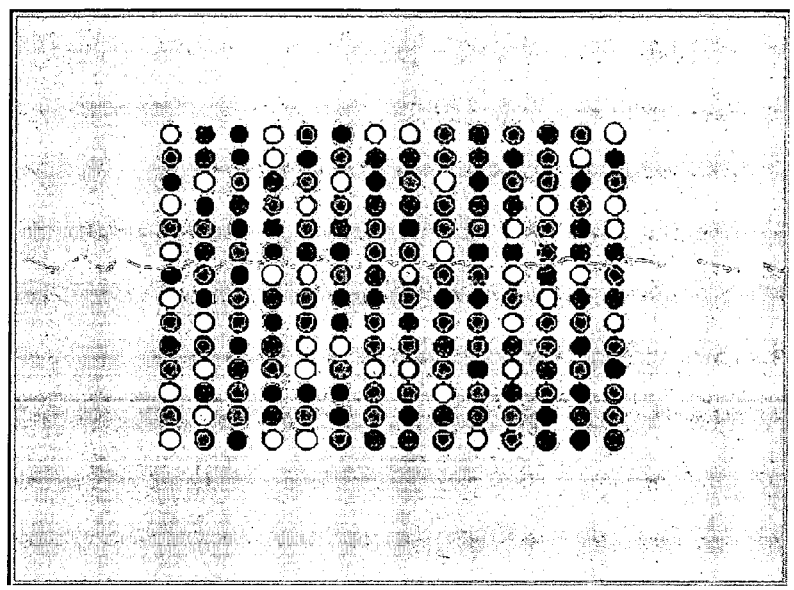
FIG. 3 illustrates a diagram indicating relevant genetic markers.

FIG. 3 is a diagram indicating a group of genetic markers that are relevant to a particular user's query on a disease or malady, organ or tissue or regulatory system, or other health- or medical-related issue. The genetic markers may be displayed in an ordered linear array or as an ordered array on a two-dimensional surface, and the relevant markers are displayed in a color or texture that is distinguishable from the remaining markers.

Figure 4:
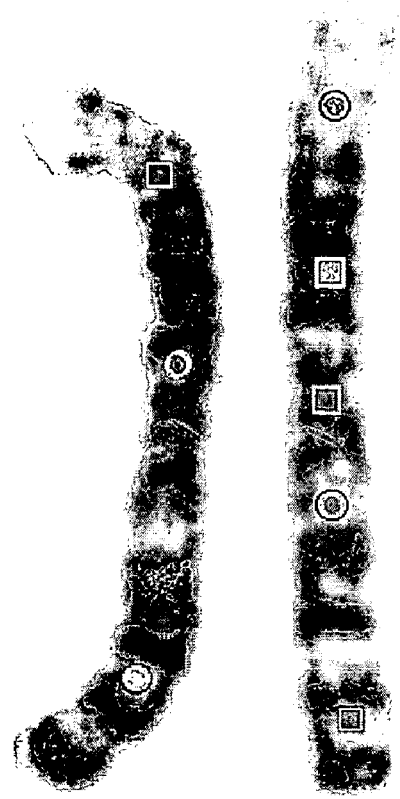
FIG. 4 illustrates a particular human chromosome and some genetic markers associated with that chromosome.

FIG. 4 illustrates a particular human chromosome (No. 19 in this Figure), with small squares indicating the location of genetic markers (for parents P1 and P2) that are relevant to a particular query from each parent. The differently shaded bands in FIG. 4 indicate gene locations that "code" for susceptibility to different maladies, including the following: colon cancer; factor V Leiden mutation; hemochromatosis; and malignant hyperthermia; and melanoma.

A key feature in any security architecture is its access control methodology. This mechanism controls who has access to what data and, when combined with privilege allocation, what the recipient can do with that data. Establishing access for users involves user authentication that is a means of verifying the user's asserted identity. Authentication can be single factor or, preferably, multi-factor. A factor is preferably something known to the user (a user ID and password), something the user possesses (a token), and/or one or more biometric indicia (fingerprints, iris scans, retinal scans, facial patterns, vein patterns, voiceprints, rapid DNA analysis, handwriting analysis and recognition, etc.). Authentication is improved when multiple authentication factors are used together.

The use of the Identifier as part of an authentication process represents a unique opportunity to combine token systems with biometrics. This combination provides ease of use and increased security system performance in that fewer authentication process steps are required for higher levels of trust. Further, the Identifier represents a unique form of identifier for the individual. Preferably, the identifier is rendered in a binary format so that can be transmitted to a personal digital assistant (PDA) device for performing portable and/or remote identification.

Once the testing has been performed, data are processed in accordance with the invention to allow the genetically profiled user to access and navigate through visual spatial representation of the data.

The graphic representations of the user's genetic profile data, and a physical location in the human body associated with such data, can be generated and displayed using geographic information systems (GIS) technology, whereby a vector graphic is programmatically linked to a record in a relational database. Examples of such technology are Autodesk MapGuide software or Oracle Spatial 8i. The software user interface will be modified for genetic and anatomical terminology.

A user can pan and zoom through a visual representation of the various chromosomes, genes, SNPs, or nucleotide sequences. The user can double click on any of these entities to initiate a selected event, such as launching a URL with additional text information or display of a visual representation of how the genetic entities correlate with effects in different organs, tissues and regulatory systems of the body.

Genes and genetic markers have three-dimensional coordinates. However, when the human genome was mapped, the sequence of nucleotides (primary structure) is specified but not the actual physical, three-dimensional location of each nucleotide (secondary and tertiary structure). Unless and until the actual physical, three-dimensional locations of the nucleotides are determined or provided, the present invention assigns genetic markers and genes to an (x,y) or (x,y,z) coordinate system. In a preferred embodiment this can be done by creating a map that specifies the physical location of each chromosome (based on a photomicrograph of a human cell in metaphase) and places the sequence information for each chromosome beneath that image. This is a simplification of where each nucleotide resides, in relation to others, but still allows for some spatial analysis, and more importantly provides a mechanism for distributing and managing an otherwise cumbersome dataset.

At this point, one has an overview map (photograph) to scale based on the amount of sequence data that lies beneath the image. The image is spatially referenced and scaled using a Tiff world file format; the raster image is later used as a background image within the MapGuide application.

The length of the longest chromosome, chromosome 1, is estimated to be 278,691,924 base pairs (mapping units). One can estimate the extent of the image to be 4.75× the transverse diameter of chromosome 1 across, or 1,323,786, 639 units across. Where a representative is 360×365 pixels, the transverse resolution would be 3,677,185 units per pixel. On that basis one can create a .TFW file to spatially reference the image. The .TFW file is an ASCII text file containing at least six lines of information:

Line 1: X resolution dimension of a pixel in map units (1 unit=1 base pair) in the X direction=3,677,185.

Line 2: Amount of translation. (standard value zero)

Line 3: Amount of rotation.

Line 4: Negative of the Y resolution dimension of a pixel in map units (1 unit=1 base pair) in the Y direction.

Line 5: X coordinate of the center of pixel 1.1 (upper-left)=5*3,677,185=1838593.

Line 6: Y coordinate of the center of pixel 1,1 (upper-left)=(365*3,677,185)−1838593=1340333972.

In order to spatially-reference a photomicrograph image of a somatic cell, specification of six numbers is required. An example is:

+3677185.00

−00.00

−00.00

−3677185.00

1838593.00

1340333972

A .TFW file has the same name as the TIFF file it references and is located in the same folder as the source file. An example is:

photomicrograph.tif photomicrograph.tfw

Next, the spatially referenced image is imported into a program such as Autocad Map and a baseline vector line segment is drawn down the middle of each chromosomes, starting from the p arm telomere of the chromosome; the direction of the line segment is of significance for subsequent topological analysis. One then calculates the relative displacement for the genetic loci values for the chromosomes so that a locus corresponds to a line segment that extends beneath the visual outline for each chromosome, and the sequence data for the corresponding chromosome segment are laid on top of that line.

The x and/or y and/or z coordinate values generated in certain calculations, discussed in the following, are exported with loci as records in a table which is then linked to it's associated genetic information, (i.e. values used for a tooltip, thematic representation or url for the given genetic marker).

A sample table for an ODBC data source is as follows

| Key | Disease | Gene | Chromosome | Starting_BasePair | URL | Secondary X | Secondary Y |
|---|---|---|---|---|---|---|---|
| NM 000410 | Hemochromatosis | HFE | 6 | 29165296 | http://www.any.html | 956587139 | 724196265 |
| NM 000038 | Colon Cancer | APC | 5 | 119602162 | http://www.any.html | 785286552 | 1147943203 |
| NM 014885 | Colon Cancer | APC10 | 4 | 154750645 | http://www.any.html | 457943103 | 667513431 |
| NM 016237 | Colon Cancer | APC5 | 12 | 133077128 | http://www.any.html | 1217584431 | 452284552 |
| NM 005883 | Colon Cancer | APCL | 19 | 587139 | http://www.any.html | 311487705 | 954750545 |
| NM 001639 | Colon Cancer | APCS | 1 | 179676945 | http://www.any.html | 719652162 | 863777528 |
| NM 000251 | Colon Cancer | MSH2 | 2 | 48943103 | http://www.any.html | 261135363 | 1349376545 |
| NM 000077 | Melanoma | CDKN2A | 9 | 24196215 | http://www.any.html | 679676345 | 829168256 |

These tabular data above are used to create the .sdf layers in the MapGuide application and thematically displayed by diseases. Values used to create the MapGuide ODBC SDF layer are as follows:
  Key: Key Column
  Tooltip: Gene
  X: Secondary X value
  Y: Secondary Y value By combining the spatially referenced raster image with the ODBC data source vector data, the user can navigate within and perform spatial queries on a physical representation of the genetic data.

Once the (x,y,z) coordinates have been determined for a series of markers, a translator can be created, using the standard unique identifiers for the various genetic markers (e.g., from the publicly available NIH datasets). As a result, the process of automating the visual display of massive genetic datasets can be achieved with minimal time and effort.

Large genetic data sets can be managed via various sub-layers (e.g., part of layers 3 and 4 in FIG. 2) that turn on and off at different pan and zoom scales to provide an optimal amount of detail at each scale. Additionally, different sub-layers of the representation can be pulled from an unlimited number of servers to optimize performance and scalability.

The genetic information on the site can be accessible from a plurality, preferably at least three, of different, interconnected mechanisms: standard text, a visual representation of the human body, and a visual representation of physical genetic entities (i.e., a cell with chromosomes, genes, protein expressions, SNP markers, and nucleotide sequences).

Information distribution mechanisms include the following.

1. Standard Text Query. Here standard text input or pull-down menu controls launch an SQL query for genetic information as a basis of disease, key words or physical location on the body or chromosomes.

2. Query Generated from Representation of a Human Body. A visual representation of the human body, whereby the user is able to pan and zoom down through the physical representation and to double click on one or more components of the body to trigger display of additional genetic information (provided in text form or in the form of a visual representation of the genes and chromosomes in the body that correlate to that physical location on the body).

As illustrations, such information mechanisms would interact as follows. If a user wishes to know about Hemochromatosis (HFE), the user selects HFE from a pull down menu on diseases. This causes the system to submit a query for a graphic representation of the human body and/or of human genes.

In a graphical representation of the human body, those areas affected by the specified disease are highlighted, identified via tool tip on a mouse over an event and each graphic entity capable of launching a URL with additional information on the disease. Data on a human body are available from the NIH's website. The detailed drawings of the body are converted to JPEG (compressed) images with the resolution optimized for different zoom scales. Organs, tissues, regulatory systems, and physical features have a vector outline with transparent fills so that the graphics are interactive but artistic renderings.

For graphic representation of a cell, the genetic information contained in the chromosomes affected by a specified disease are highlighted, identified via tool tip on a mouse over event, with each graphic entity being capable of launching a URL with additional information on the disease. Different types of information would be available at different zoom scales (chromosome down to the level of nucleotide sequence and allelic variants). Additionally, using the MapGuide API, a series of tools can be created to enable the user to perform topological analysis (the ability to draw a polygon to select a group of objects with the keys from the selected objects passed on to generate a report).

For MapGuide, the applications depicting the human body and/or human genes are preferably part of a special mime type .mwf file that is embedded in the frame of the html as follows:

<OBJECT ID="myMap"WIDTH=300 HEIGHT=200
  CLASSID="CLSID:62789780-B744-11D0-986B-
    00609731A21D">
  <PARAM NAME="URL" VALUE="http://www.dominga.com/maps/0244.mwf">
  <EMBED SRC="http://www.dominga.com/maps/0244.mwf" NAME="myMap" WIDTH=300 HEIGHT=200>
  </OBJECT>

This .mwf file is passed by the network server to a MapGuide agent, which runs as a separate service on top of an NT server. The .mwf file includes pointers to different layers of information that are available from any networked server, thus providing extended scalability. In the case of Oracle Spatial 8i, the links between the graphic entities and relational database would be set up using JDBC. The raster image information can, for example, be served up using Lizard compression technology with .ric files in MapGuide. In the case of Oracle, globs are used to serve up the background renderings for the images.

One feature of the software applications security mechanism is the ability of the data owner (the individual submitting the sample) to set up time-sensitive user accounts to share the owner's medical information with his/her doctor, etc. as they determine to be in their own self-interest. In such cases, user account privileges can be set up within MapGuide and tied to either zoom scales, layers or at the vector entity level, in addition to normal security functionality present at the network, web server and data source level (i.e., as provided by Oracle).

For example, by creating a series of pull-down menus using Cold Fusion or ASP to trigger events tied to the MapGuide API (i.e., turning on and off layers of data and passing the access key for only the visible objects or layer), the genetic data owner can customize the security related to his/her personal data.

Upon log-in, MapGuide will prompt a physician or other health care professional for an access code in order to view a limited dataset (as specified or limited by the end user). Communication between a specific user and the data owner regarding the information is preferably handled via an anonymous e-mail account.

A subsequent and related feature of the software security mechanism is the ability of the data owner to specify that his/her personal data be destroyed (either in part or in entirety). Hence, as described above, the user can specify layers information or specific markers for which the user wishes selected personal data to be destroyed or deleted as part of the MapGuide interface.

A Process for Calculating (x,y,z) Coordinates

Consider a DNA (or RNA) chain, illustrated in FIG. 5, that contains one or more representatives of chromosomes as a linear chain CH of N+1 molecular constituents, such as nucleotides with an associated sugar-phosphate backbone (the backbone is ignored as part of the linear chain structure, except for its effects on the secondary and tertiary structure, discussed below). Assume that a free end of this chain CH (e.g., location of a telomere or other selected atomic or molecular constituent) is located at an origin O of a Cartesian coordinate system and that any two consecutive molecular constituents, numbered n and n+1 (n=1, . . . , N) in the chain are connected by a constituent-to-constituent bond of length $L_n$. Each link n is initially aligned parallel to a z-axis of the coordinate system. The primary structure of the chain CH is that of N+1 molecular chain constituents, joined end-to-end and aligned parallel to a selected axis (e.g., the x-axis), with constituents n and n+1 being joined by a link of length $L_n$.

One by one, beginning with the constituent numbered n=1, the initial alignment is relaxed so that each link assumes an orientation relative to the preceding link that is determined by the constituent-to-constituent individual and collective interactions, to produce a secondary structure (and possibly a tertiary structure and/or a quaternary structure) that may have a helical or another substantially linear structure. Relative to a direction defined by the orientation of link number n (considered as a local x-axis), the normalized coordinates $(x_{n-1}, y_{n-1}, z_{n-1})$ with $x_{n-1}^2 + y_{n-1}^2 + z_{n-1}^2 = 1$, of the second end (far end) of link number n+1 relative to the near end of this link are given by a matrix relationship:

$$X_{n-1} = R(\phi_{n-1}, \theta_{n-1}) X_n, \quad (1)$$

$$X_n = \begin{vmatrix} x_n \\ y_n \\ z_n \end{vmatrix}, \quad (2)$$

$$R(\phi_n, \theta_n) = \begin{vmatrix} \cos\phi_n \cos\theta_n & \sin\phi_n \cos\theta_n & \sin\theta_n \\ -\sin\phi_n & \cos\phi_{n-1} & 0 \\ -\cos\phi_n \sin\theta_n & -\sin\phi_n \sin\theta_n & \cos\theta_n \end{vmatrix} = R_n \quad (3)$$

Figure 5:
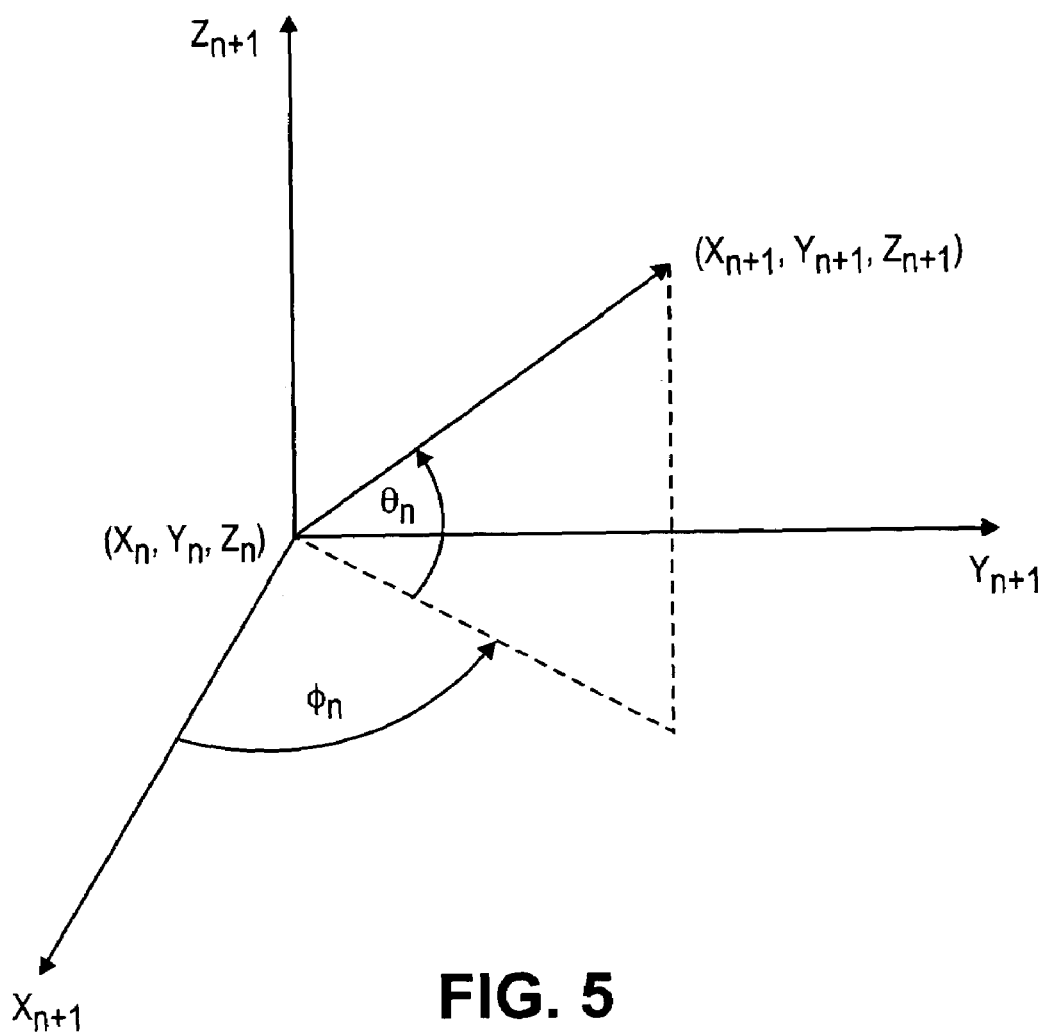
FIGS. 5 and 6 illustrate spatial relationships of consecutive molecular constituents in a chain to each other.
Figure 6:
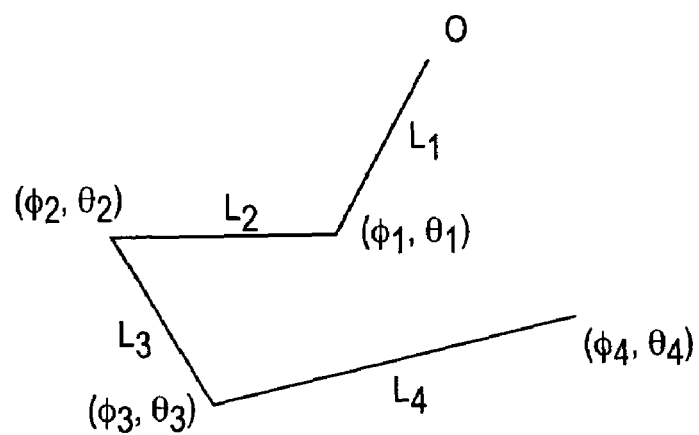

This orientation is illustrated in FIGS. 5 and 6. The non-normalized coordinates of the second end of link n+1, relative to the original coordinate system with origin O then become $$X'_{n-1} = \{L_1 PR(1) + L_2 PR(2,1) + L_3 PR(3,2,1) + \ldots + L_{n-1} PR(n+1, n, \ldots, 1)\} X_n, \quad (4)$$

$$PR(n+1, n, \ldots, 1) = R(\phi_{n-1}, \theta_{n-1}) PR(n, n-1, \ldots, 1), \quad (5)$$

$$PR(1) = R(\phi_1, \theta_1). \quad (6)$$

The link lengths $L_n$ may be, but need not be, the same. For example, it is generally accepted that the distance between two consecutive base pairs in a DNA helix is about 0.34 nanometers (nm), under normal cellular conditions of temperature and ionic strength, but this number represents an average or mean value, not a fixed and immutable distance.

Computation of the coordinates of $X'_{n-1}$, given a knowledge of the angles $\phi_k$ and $\theta_k$ (k=1 . . . , n+1), is straightforward but time consuming, even where the orientation angles $\phi_k$ and $\theta_k$ are all known or prescribed. This task can be made simpler by the following approach: for a sequence of spaced apart integers n=n1, n2 (>>n1), n3 (>>n2), . . . , compute and store the coordinates $X'_n$, for n=n1, n2, n3, . . . For any integer m satisfying nq<m<n(q+1), use the stored quantities $X'_{nq}$ and Eqs. (4) to generate $X'_m$, beginning with the known quantity $X'_{nq}$. The integer differences n(q+1)−nq can be as small as 5–10, or some larger range of numbers, such as 20–100 or 200–800 or 500–1000 or larger. These integer differences need not be uniform.

The link-to-link polar angles $\theta_k$ ($0 < \theta_k < \pi$) can be treated as approximately fixed, with a small angular variation, but the azimuthal angles $\phi_k$ may range over a full cycle ($0 < \phi_k < 2\pi$) subject to a probability density function $f(\phi_k; \theta_k; k)$ that reflects well known stereochemical angle hindrances that arise from neighbor-to-neighbor interactions between adjacent molecular constituents. For example, if the energy of interaction between the molecular constituents number k−1 and k is $E(\phi_k; \theta_k\, k)$, with $\theta_k$ approximately fixed, the probability density function can be approximated as $$f(\phi_k; \theta_k; k; T) = \exp\{-E\phi_k; \theta_k; k)/k_B T\}/\{\int \exp\{-E(\phi'; \theta_k; k)/k_B T\} d\phi'\}, \quad (7)$$

where $k_B$ is the Boltzmann constant and the density function f now depends also depends upon local temperature T. As the temperature T increases, the density function f may approach a function that has uniform amplitude in the azimuthal angle $\phi_k$.

As a first approximation, the average geometry of a DNA helix can be adopted, having ten nucleotides per full turn ($\phi_{n-1} - \phi_n = 36°$), and a bond angle $\theta_n$ and bond length $L_n$ that are related by $L_n \sin \theta n = 0.34$ nm. This first approximation can then be varied by imposing constraints that are determined from visual observations or diffraction measurements for a particular user.

What is claimed is:

1. A method for providing a personal genetic profile, comprising:
   providing genetic data for an individual, wherein the genetic data comprises associated attribute information; and
   mapping the genetic data using geographic information systems to spatially represent the genetic data in a thematic map based on the attribute information;
   providing data for at least one genetic marker associated with the individual;
   representing the at least one genetic marker at at least one location in the thematic map wherein the representation of the genetic marker comprises genetic marker data in alphanumeric format at a location adjacent to the genetic marker location;
   providing a general database, including a least one feature associated with the at least one genetic marker, for a general population of individuals; and
   receiving an Identifier associated with the individual, (1) using the Identifier to identify the individual, displaying at least one of (i) a visual representation of a selected portion of the individual's body indicating the at least one location for the at least one genetic marker, (ii) data for the at least one genetic marker associated with the individual, (iii) selected data on at least one disease associated with the at least one genetic marker, and (iv) data on at least one regulatory system associated with the at least one genetic marker, and (2) comparing data on the at least one feature associated with the at least one genetic marker from the general database with the displayed data for the individual.

2. The method of claim 1, further comprising including in said Identifier at least one biometric indicium for said individual.

3. The method of claim 2, further comprising drawing said biometric indicium from a group of biometric indicia associated with said individual and consisting of; at least one fingerprint, at lease one iris scan, at least one retinal scan, at least one facial pattern, at least one blood vein pattern; at least one voice print of said individual's voice; and at least one DNA analysis of a biometric sample received from said individual.

4. The method of claim 1, further comprising including in said Identifier a selected token associated with said individual.

5. The method of claim 1, further comprising including in said Identifier a selected password associated with said individual.

6. The method of claim 1, further comprising;
   providing said general database in a first data layer to any data user;
   providing said genetic marker data in a second data layer; and
   providing access to said individual's genetic marker data only upon presentation of said Identifier.

7. The method of claim 1, further comprising;
   providing said general database in a first data layer to any data user;
   providing said genetic marker data in a second data layer having at least a selected second data layer first sub-region and a selected second data layer second sub-region;
   providing access to said individual's genetic marker data in the second layer first sub-region only upon presentation of a first type of said Identifier; and
   providing access to said individual's genetic marker data in the second layer second sub-region only upon presentation of a second type of said Identifier.

8. The method of claim 7, further comprising configuring said second layer second sub-region of said genetic marker data to partially, but not fully, overlap said second layer second sub-region of said genetic marker data.

9. The method of claim 7, further comprising configuring said second layer first sub-region of said genetic marker data and said second layer second sub-region of said genetic marker data to have substantially no overlap.

10. The method of claim 1, further comprising representing said at least one genetic marker at at least one location in a coordinate system having at least two dimensions.

11. The method of claim 1, further comprising representing said at least one genetic marker at at least one location in a coordinate system having at least three dimensions.

12. The method of claim 1, wherein said process of representing said at least one genetic marker at said at least one selected location comprises;
   providing a primary chemical structure for a sequence of molecular constituents that are part of a DNA chain representing a biological makeup for said individual and including the selected location;
   providing a secondary chemical structure for the sequence of molecular constituents that are part of the chain;
   providing at least one value of a bond length between two consecutive molecular constituents of the chain and at least one value of a bond angle associated with two consecutive bonds between consecutive molecular constituents of the chain, where the at least one bond length and the at least one bond angle are consistent with the primary and secondary chemical structure of said molecular constituents that are part of the chain; and
   providing a quantitative matrix relationship that describes three-dimensional coordinates for each molecular constituent that is part of the chain relative to a preceding molecular constituient in the chain and that is consistent with the primary and secondary chemical structure of said molecular constituents that are part of the chain.

13. The method of claim 12, wherein said process of providing said matrix relationship comprises representing said three-dimensional coordinates $X'_{n+1} = (x_{n-1}, y_{n-1}, z_{n-1})$ for location of a molecular constituent number n+1 in terms of said three-dimensional coordinates $X'_n = (x_n, y_n, z_n)$, for location of a preceding molecular constituent number n in said chain by a relationship $$X'_{n-1} = L_n R(\phi_n, \theta_n) X_n,$$

$$R(\phi_n, v_n) = \begin{vmatrix} \cos\phi_n \cos\theta_n & \sin\phi_n \cos\theta_n & \sin\theta_n \\ -\sin\phi_n & \cos\phi_{n-1} & 0 \\ -\cos\phi_n \sin\theta_n & -\sin\phi_n \sin\theta_n & \cos\theta_n \end{vmatrix},$$

where $\phi_n$ and $\theta_n$ are selected aximuthal and polar angles, respectively, associated with the molecular constituent number n+1.

14. The method of claim 1 further comprising creating a plurality of views within the thematic map based on a zoom scale.

15. The method of claim 14 further comprising using at least one of the plurality of views to create a selection set of genetic markers for exercising security administration over said genetic data, wherein exercising security administration over said genetic data comprises destroying the genetic data.

* * * * *